United States Patent [19]

Feldman

[11] Patent Number: 4,931,052
[45] Date of Patent: Jun. 5, 1990

[54] DIAPER WITH INTEGRAL WIPING CLOTH AND DISPOSAL CONTAINER

[76] Inventor: Ruth L. Feldman, c/o Dr. Robert Plotkin 28 Brennan Dr., Bryn Mawr, Pa. 19010

[21] Appl. No.: 369,047

[22] Filed: Jun. 16, 1989

[51] Int. Cl.⁵ .............................................. A61F 13/16
[52] U.S. Cl. .................................. 604/385.1; 206/438
[58] Field of Search ..................... 604/385.1; 206/210, 206/581, 438

[56] References Cited

U.S. PATENT DOCUMENTS

| | | | |
|---|---|---|---|
| 1,608,934 | 11/1926 | Goldsmith | 206/581 |
| 2,940,449 | 6/1960 | Thomson | 206/581 |
| 3,035,578 | 5/1962 | Elmore | 604/385.1 |
| 3,889,804 | 6/1975 | Ravich | 206/581 |
| 4,085,753 | 4/1978 | Gellert | 604/385.1 |
| 4,417,894 | 11/1983 | Norris | 604/385.1 |
| 4,550,855 | 11/1985 | Harrison | 206/210 |
| 4,604,096 | 8/1986 | Dean et al. | 604/385.1 |
| 4,738,677 | 4/1988 | Foreman | 604/385.1 |
| 4,738,678 | 4/1988 | Paulis | 604/385.1 |
| 4,743,240 | 5/1988 | Powell | 604/385.1 |
| 4,753,647 | 6/1988 | Curtis | 604/385.1 |
| 4,781,712 | 11/1988 | Barabino et al. | 604/385.1 |
| 4,790,840 | 12/1988 | Cortina | 604/385.1 |
| 4,808,175 | 2/1989 | Hansen | 604/385.1 |
| 4,857,066 | 8/1989 | Allison | 206/438 |

FOREIGN PATENT DOCUMENTS 0868299  5/1961  United Kingdom ............. 604/385.1

Primary Examiner—Rosenbaum C. Fred
Assistant Examiner—Sharon Rose
Attorney, Agent, or Firm—Robert G. Rosenthal

[57] ABSTRACT

A disposable diaper with an integral wiping cloth and disposal container forming an integrated baby changing system is disclosed. The disposable diaper has a skin contacting moisture absorbing inner surface and a waterproof environment interfacing outer surface. A storage container means is mounted to the outer surface of the diaper and includes a liquid impermeable membrance formed so as to define a sulable pocket for retaining a towelette therein in the moistened state until such time as the towelette is needed for wiping the skin. The pocket is expandable to form a disposal container for the soiled diaper and the spent towelette. A moist towelette is adapted to be stored within the storage container means.

11 Claims, 4 Drawing Sheets

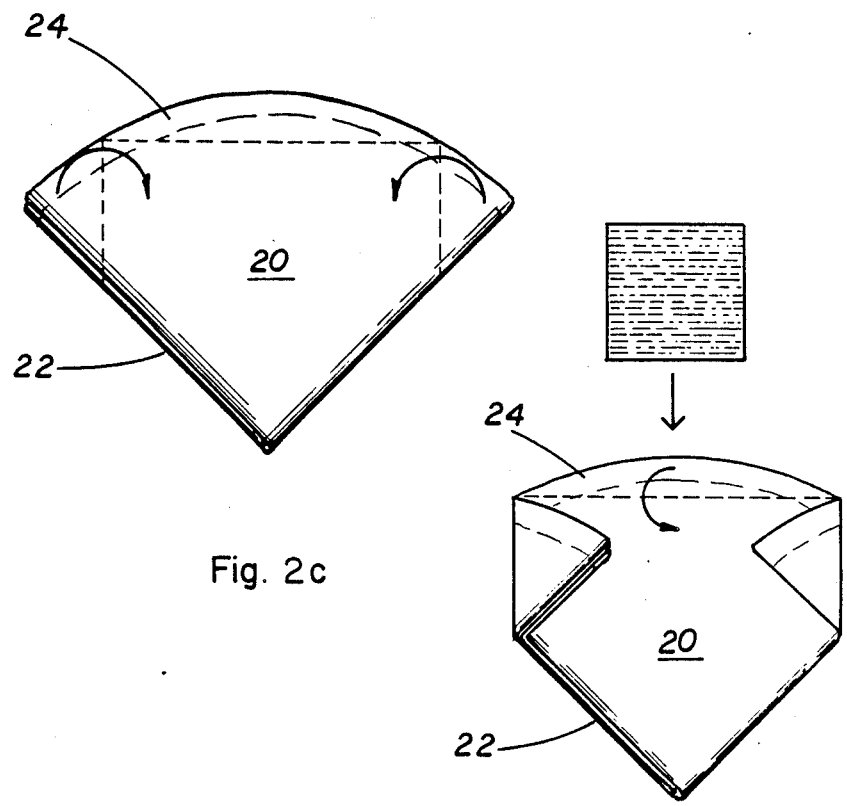
Fig. 2c
Fig. 2d
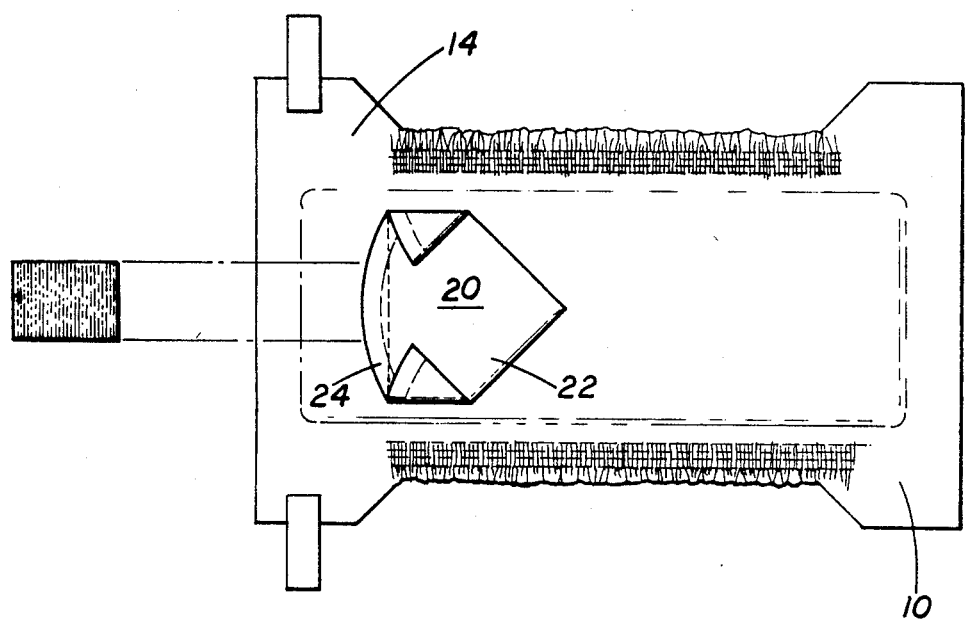
Fig. 3

DIAPER WITH INTEGRAL WIPING CLOTH AND DISPOSAL CONTAINER

FIELD OF THE INVENTION

This invention relates generally to the field of disposable diapers and more specifically to the field of diapers that include an integral wiping cloth and disposal container.

BACKGROUND OF THE INVENTION

Disposable infant diapers are well known as are moistened towelettes and disposal bags. Under normal home conditions, these items are normally found in the home nursery and it is usually not a problem to change a soiled diaper, the normal required materials being a clean fresh diaper, a number of moist towels or disposable towelettes and a disposal container. However, when traveling with a child, transporting the above noted items in a changing bag or other type of container can become troublesome. None of the aforementioned items is overly burdensome to transport individually, however, collectively, the entire grouping can be difficult to transport due to its bulkiness and weight.

In view of the foregoing, it is an object of the present invention to provide a baby changing system which is lightweight and compact.

It is another object of the present invention to provide a baby changing system which is easily transportable.

It is still another object of the present invention to provide a baby changing system which is easily disposable.

It is yet another object of the present invention to provide a baby changing system which includes all of the necessities required to change a baby in a single item.

SUMMARY OF THE INVENTION

In accordance with the present invention, there is provided a disposable diaper, wipe and disposal container forming a integrated baby changing system. The disposable diaper has a skin contacting moisture absorbing inner surface and a waterproof environment interfacing outer surface. A disposal container means is mounted to the outer surface of the diaper and includes a liquid impermeable membrane formed so as to define a sealable pocket for retaining a towelette therein in the moistened state until such time as the towelette is needed for wiping the skin. The pocket is expandable to form a disposal container for the soiled diaper and the spent towelette. A moist towelette is adapted to be stored within the storage container means.

BRIEF DESCRIPTION OF THE DRAWINGS

Some of the objects of the invention having been stated, other objects will appear as the description proceeds when taken in connection with the accompanying drawings in which:

FIG. 2c is a plan view showing the pocket being formed.

FIG. 2d is a plan view of the completed pocket.

FIG. 3 is a plan view of a diaper with the storage container means being connected thereto and the moistened towelette being inserted therein.

DETAILED DESCRIPTION OF THE ILLUSTRATED EMBODIMENT

While the present invention will be described more fully hereinafter, it is to be understood at the outset that persons of skill in the art may modify the invention herein described while still achieving the favorable results of the invention. Accordingly, the description which follows is to be understood as a broad teaching disclosure directed to persons of skill in the appropriate arts, and not as limiting upon the present invention.

Figure 1:
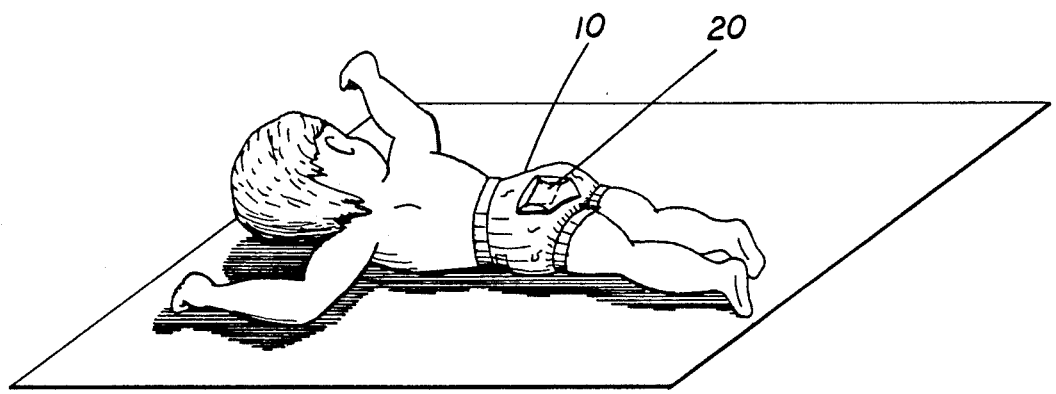
FIG. 1 is a perspective view of a child wearing the baby changing system of the present invention.

Referring more specifically to the drawings, and particularly to FIG. 1, the baby changing system is shown being worn by an infant. In general, a diaper 10 of convention construction is employed. The diaper 10 includes a skin contacting moisture absorbing inner surface 12 and a waterproof environment interfacing outer surface 14 with a moisture absorbing material sandwiched therebetween.

Figure 4:
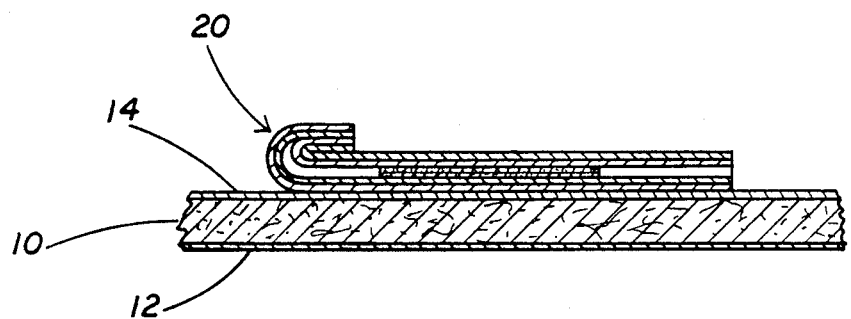
FIG. 4 is a side view taken in section of the diaper with the storage container means connected thereto and housing the moistened towelette.
Figure 5:
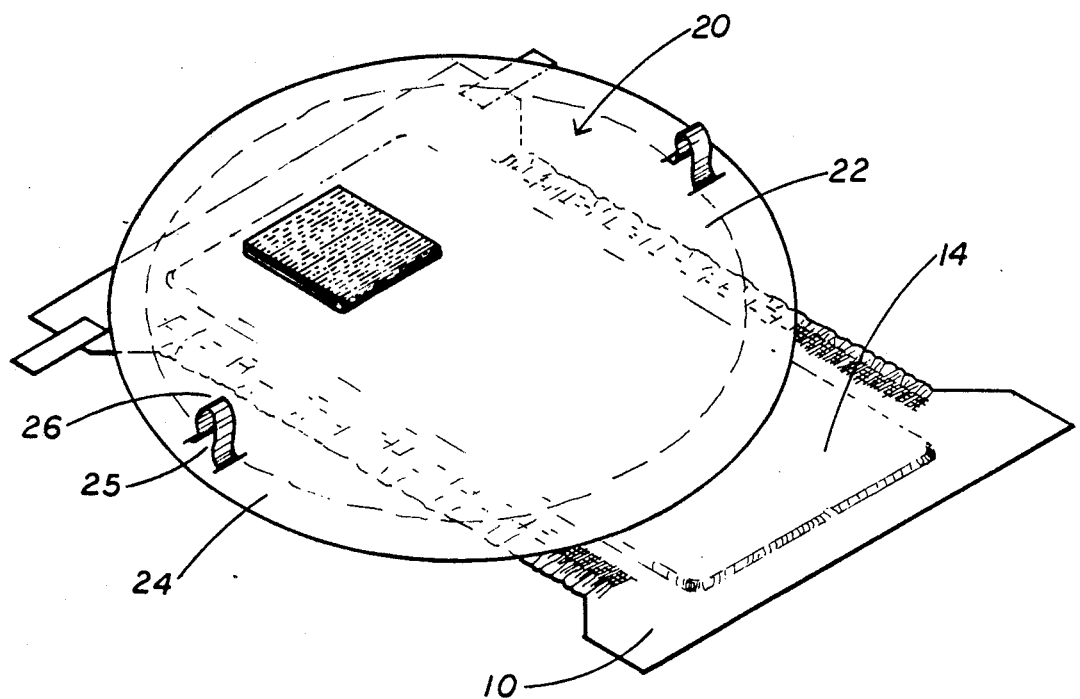
FIG. 5 is a perspective view showing the storage container means opened with the towelette being positioned thereon.

As shown in FIGS. 3 through 5, a storage container means or storage container generally indicated at 20 is mounted via suitable means such as glue or fusion to the outer surface of the diaper 10 (as best shown in FIG. 3). The storage container means 20 takes the form of a liquid impermeable membrane 22 which is formed into a sealable pocket for retaining a towelette therein in the moistened state. When it is desired to use the towelette for wiping the skin, the pocket is opened and the towelette is removed therefrom. As shown in FIG. 5, the pocket expands and forms a disposal container for the soiled diaper and the spent towelette.

The liquid impermeable membrane in the illustrated embodiment takes the form of a circular plastic disk and includes a hem 24 located proximate its outer peripheral edge. A drawstring or string 26 is provided and is slidably mounted within the hem 24. The hem 24 also includes a pair of oppositely positioned cut out portions 25 for providing ease of access to the drawstring 26 which may also contain a scent or deodorant.

Figure 2A:
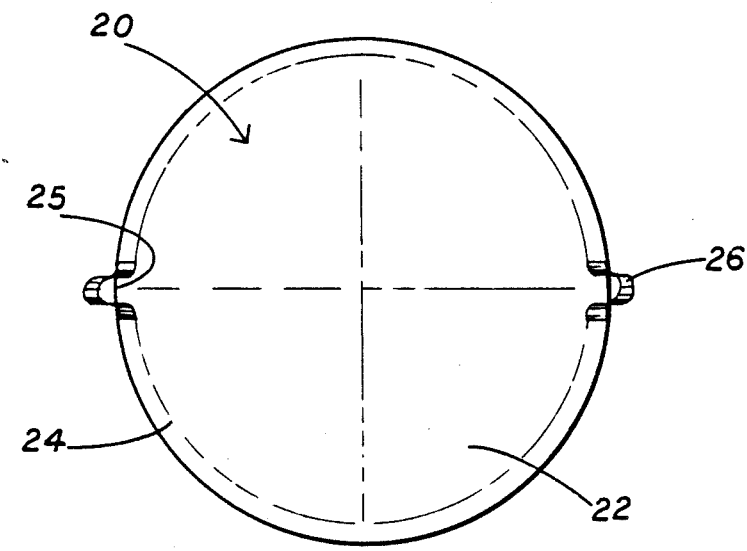
FIG. 2a is a plan view of the storage container means prior to being folded into a pocket.
Figure 2B:
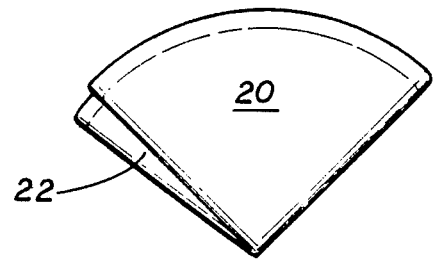
FIG. 2b is a plan view, taken in perspective of the storage container means being folded into a cone.

FIGS. 2a through illustrate the formation of the storage container means 20. First, a substantially circular plastic disk (FIG. 2a) is folded into a cone shape (FIG. 2b). Then the edges of the cone are folded inward and may be held in place by a suitable light adhesive or fusion process which will not interfere with the opening of the pocket. Next, the towelette is inserted into the pocket and finally, the top flap is folded down and is similarly held in place by a light adhesive (FIG. 2c). The completed pocket is illustrated in FIG. 2d. The edges of the cone may also be tucked inside forming pleats for a neater looking pocket.

Figure 6:
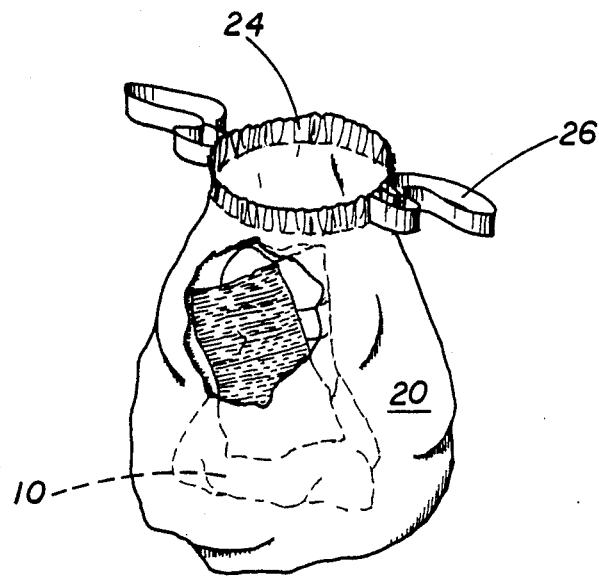
FIG. 6 is a perspective view of the storage container means inverted showing the spent diaper and used towelette stored therein.

In use, the storage container means 20 is secured to the outer surface 14 of the diaper 10 so as to overlie the child's buttox as shown in FIG. 1 until such time as the towelette is needed for wiping the skin. When the diaper becomes soiled, it is removed from the child and the storage container means is then opened and the towelette is removed. The child is cleaned and the storage container means 20 is opened so as to receive the soiled diaper and the towelette. As best shown in FIG. 6, the entire package is then closed by pulling the drawstring 26.

It will be noted that the storage container means as shown in FIG. 2d may be employed as a diaper disposal and child clean-up system separate and apart from the diaper, and thus, may be sold individually. Of course, the pocket may contain a varying number of towelettes and the storage container means 20 may also include a visual indicator means, such as a colored adhesive-backed strip which may be used to close the pocket flap and which indicates the number of towelettes contained in the pocket. In this manner, the parent can choose an appropriate pocket depending on the extent to which the diaper may be soiled. Pockets sold in this manner will contain a suitable adhesive backing for attaching to the diaper.

Throughout this specification the word diaper has been used in conjunction with infants. However, it will be noted that the concept may easily be extened to sanitary napkins and to larger size diapers such as might be worn by incontinent or otherwise infirmed adults.

In the drawings and specification, there has been set forth a preferred embodiment of the invention, and although specific terms are employed, they are used in a genuine and descriptive sense only and not for purposes of limitation.

That which is claimed is:

1. A disposable diaper, wipe, and disposal container, forming an integrated baby changing system comprising:
    a disposable diaper having a skin contacting moisture absorbing inner surface and a waterproof environment interfacing outer surface;
    a storage container means mounted to the outer surface of said diaper and comprising a liquid impermeable membrane folded so as to define a sealable pocket for retaining a towelette therein in the moistened state until such time as the towelette is needed for wiping the skin, and said pocket adapted to expand and to form a disposal bag for said soiled diaper and the spent towelette; and
    a hem proximate the outer peripheral edge of said membrane;
    a closure means slidably positioned within said hem for closing said storage container means; and
    a moist towelette adapted to be stored within said storage container means.

2. The baby changing system according to claim 1 wherein said liquid impermeable membrane includes a closure means positioned proximate the outer peripheral edge of said storage container means.

3. The baby changing system according to claim 2 wherein said storage container means comprises a substantially circular disk that includes a hem and wherein said closure means is slidably positioned within said hem.

4. The baby changing system of claim 1 wherein said storage container means is adapted to encircle and enclose the spent diaper.

5. The baby changing system of claim 2 wherein said closure means contains a deodorant to absorb odors from the spent diaper.

6. The baby changing system of claim 2 wherein said closure means comprises a string.

7. A disposable diaper, wipe and disposal container forming an integrated baby changing system comprising:
    a disposable diaper having a skin contacting moisture absorbing inner surface and a waterproof environment interfacing outer surface;
    a storage container means mounted to the outer surface of said diaper and comprising a liquid impermeable membrane in the form of a circular plastic disk folded into a cone and defining a sealable pocket for retaining a towelette in the moistened state therein until such time as it is needed for wiping the skin, and said pocket being adapted to expand and to form a disposal container for said soiled diaper and the spent towelette when inverted,
    a hem proximate the outer peripheral edge of said plastic disk;
    a closure means slidably positioned within said hem for closing said container means; and
    a moist towelette adapted to be stored within the storage container means, whereby the storage container means retains the towelette in the moistened state when the diaper is in use and is expandable to form a disposal container and to encircle spent diaper when inverted.

8. A attachment for a diaper of the type having a skin contacting moisture absorbing inner surface and a waterproof environment interfacing outer surface of the type which is commonly worn by infants and comprising:
    a storage container means mounted to the outer surface of said diaper, said storage container means comprising a liquid impermeable membrane folded so as to define a sealed pocket and adapted to retain therein a towelette in the moistened state until such time as it is needed for wiping the skin, and said pocket being adapted to be opened and to expand to form a disposal container for said soiled diaper and the spent towelette,
    a hem proximate the outer peripheral edge of said membrane;
    a closure means slidably positioned within said hem for closing said storage container means; and
    a moist towelette adapted to be stored within said storage container means.

9. An attachment for a diaper according to claim 8 further including adhesive means for attaching said storage container means to the outer surface of said diaper.

10. An attachment for a diaper according to claim 8 wherein said storage container means is adapted to receive a plurality of moist towelettes.

11. An attachment for a diaper according to claim 10 further including visual indicator means for indicating the number of towelettes contained within the storage container means.

* * * * *